United States Patent [19]
Weissman

[11] Patent Number: 4,758,159
[45] Date of Patent: Jul. 19, 1988

[54] ADJUSTABLE MANDREL

[75] Inventor: Bernard Weissman, New York, N.Y.

[73] Assignee: IPCO Corporation, White Plains, N.Y.

[21] Appl. No.: 915,395

[22] Filed: Oct. 6, 1986

[51] Int. Cl.[4] ............................................. A61C 3/00
[52] U.S. Cl. ..................... 433/161; 433/49; 433/75; 269/244; 269/247
[58] Field of Search .................... 433/75, 76, 49, 50, 433/53, 139, 153, 163, 161, 158; 269/244, 240, 241, 242, 243, 245, 246, 247, 257, 270

[56] References Cited

U.S. PATENT DOCUMENTS

| | | | |
|---|---|---|---|
| 788,716 | 5/1905 | Hammond et al. | 269/244 |
| 1,740,238 | 12/1929 | Gustafson | 269/244 |
| 2,398,941 | 4/1946 | Jordan | 269/244 |
| 2,716,911 | 9/1955 | Focke | 269/247 |
| 3,580,459 | 5/1971 | Gage et al. | 269/242 |
| 3,722,098 | 3/1973 | Poveromo | 433/161 |
| 4,348,181 | 9/1982 | Dawson | 433/172 |

FOREIGN PATENT DOCUMENTS 376092 6/1973 U.S.S.R. ............................ 433/153

Primary Examiner—John J. Wilson
Attorney, Agent, or Firm—Goodman & Teitelbaum

[57] ABSTRACT

An adjustable mandrel for grasping and supporting a workpiece such as a dental retention device. The mandrel includes a stationary jaw having a body portion with a dependent grasping leg, and a movable jaw also having a body portion with a depending grasping leg. The two grasping legs are arranged to each other. A captured screw member is rotatably secured to the body portion of the stationary jaw with the body portion of the movable jaw threadingly receiving the screw member therethrough. A pair of guide rails maintain a parallel relationship between the stationary and movable jaws. As the screw member is rotated, the movable jaw moves into and out of engagement with the stationary jaw to grasp a workpiece with the grasping legs, where either external or internal surfaces of the workpiece can be grasped.

7 Claims, 2 Drawing Sheets

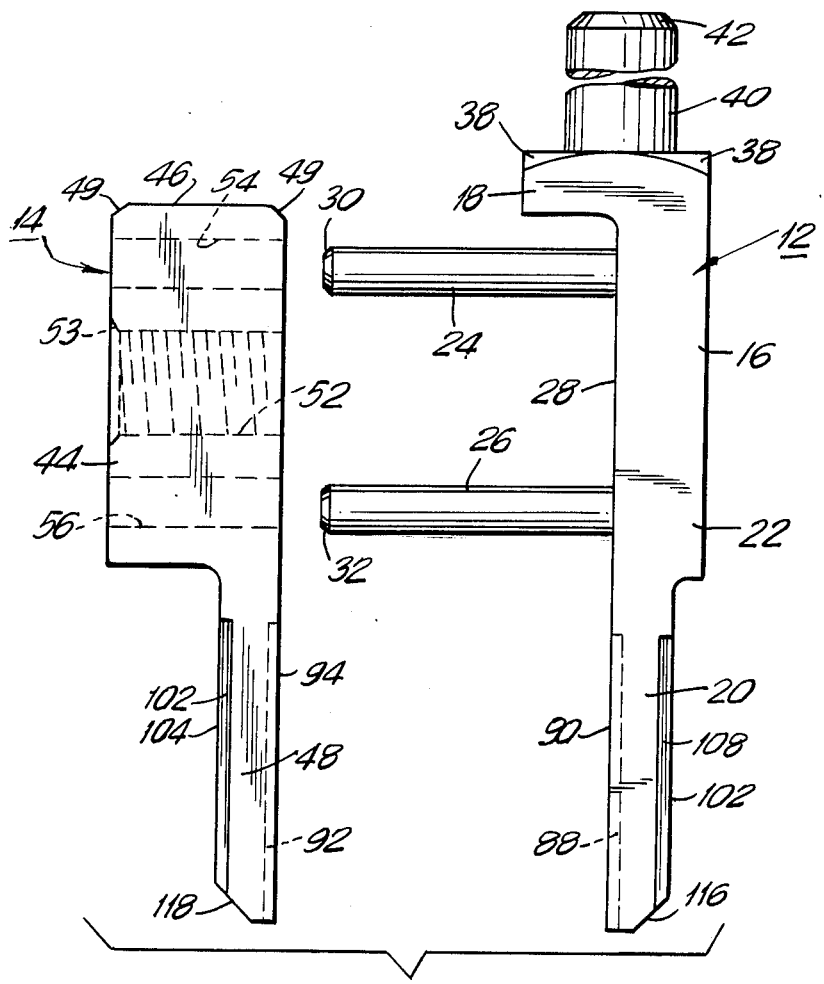
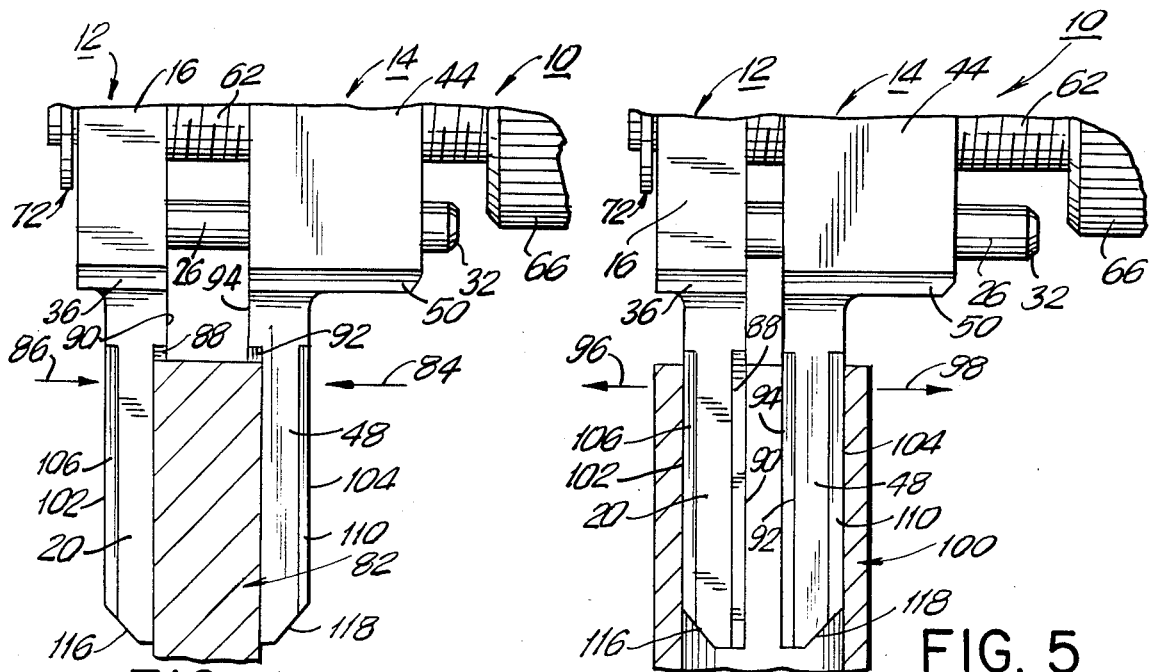
FIG. 3
FIG. 4
FIG. 5

ADJUSTABLE MANDREL

BACKGROUND OF THE INVENTION

This invention relates to an adjustable mandrel for holding a workpiece, and more particularly, to a mandrel which can be utilized for positioning dental retaining members which are used to removably secure a dental prosthesis.

Adjustable mandrels are utilized for grasping workpieces and securely holding them in place during positioning or placement of the workpiece. Often, the workpiece must be maintained in parallel relationship with a mating workpiece, and the adjustable mandrel must be capable of such parallel placement. Additionally, the workpieces may include parallel surfaces, and the grasping portions of the mandrel should be able to engage these parallel surfaces with equal distribution of force, while avoiding angular grasping along these parallel surfaces.

Such an adjustable mandrel is used in connection with the positioning of dental retaining devices used in the formation of a dental prosthesis. Such dental retaining devices are described in U.S. Pat. Nos. 4,996,516 and 4,348,181. In both of these patents, there are described retaining devices having male and female sections. One of these sections is secured to the side of a fixed tooth while the mating section is secured within a dental prosthesis. One of these sections includes a projection which is received by the other section. A spring loaded member retains the two sections in locking engagement while permitting separation of the dental prosthesis from the fixed teeth. In order to achieve an accurate fit of the dental prosthesis, a suitable tool must be utilized for placing the mating sections in proper spaced relationship and in proper parallel alignment. Generally, the tool would grasp the section and align it in parallel relationship with the other section. Appropriate dental casting techniques would be then used to form the dental prosthesis with the sections cast in place. Thus, proper grasping and retention of the sections in parallel alignment is of critical importance in forming this dental prosthesis.

One type of grasping mandrel is described in the aforementioned U.S. Pat. No. 4,348,181. Such mandrel device is described as a jig having an elongated body which includes a longitudinal slot extending from a free end of the body to define a pair of bifurcated legs. At the free ends of the bifurcated legs, portions of the legs are cut away to define an inverted U-shaped grasping section which is wider than the elongated slot and serves to grasp portions of the dental retaining device sections therebetween. A clamping screw extends through the bifurcated legs and across the slot. The screw can be tightened to bring the legs together thereby clamping the dental retaining device section between the inverted U-shaped grasping section at the free ends of the legs.

While such mandrel has been found useful, it has been noted that the grasping portion at the end of the legs does not provide accurate parallel grasping along the entire length of the dental retaining device section. Since the grasping portion is at the end of the bifurcated legs, the legs are actually pivoted with respect to each other from a common hinge point. By clamping together the two legs, the legs are actually angularly brought adjacent to each other and fail to maintain their parallel relationship. This is especially a problem when utilizing a jig having an elongated body portion, where the longer the length, the greater the deviation from a parallel relationship.

Additionally, although the leg portions of the described jig may be extensive, the retaining portion is only at the tip where the widened inverted U-shaped slot is provided. Thus, the only retention force on the dental workpiece is at a rather short retention point rather than along the entire body portion of the workpiece. An insufficient path or engagement thereby occurs with such a short retention point on the workpiece.

Although the dental retaining device male section can be grasped between the legs, the mating dental retaining device female section includes an oval shaped part, where grasping of the oval shaped part about its exterior surface becomes difficult. A better method for retention of the female section would be to grasp the oval portion interiorly. However, the aforementioned jig only provides grasping from the outside of the workpiece.

Accordingly, while the known device for grasping such dental pieces has been useful, improvements would appear warranted to enhance its capabilities and expend its utilization for retaining dental attachments.

SUMMARY OF THE INVENTION

Accordingly, it is an object of the present invention to provide an adjustable mandrel which avoids the aforementioned problems of the prior devices.

A further object of the present invention is to provide an adjustable mandrel which can be used to grasp a dental workpiece about its exterior or from its interior.

Yet another object of the present invention is to provide an adjustable mandrel which can maintain an accurate parallel relationship between its grasping legs thoughout the adjustment capabilities of the mandrel.

Still a further object of the present invention is to provide an adjustable mandrel which provides a long path of engagement between the grasping legs of the mandrel and the surfaces of the workpiece being retained.

A further object of the present invention is to provide an adjustable mandrel which can be easily manipulated to grasp a workpiece placed between its grasping legs, or positioned around the grasping legs of the mandrel.

Still another object of the present is to provide an adjustable mandrel having grasping legs which facilitate grasping an arcuate workpiece, by approximating the interior curvature of the workpiece.

Yet another object of the present invention is to provide an adjustable mandrel having a pair of grasping legs which accurately grasp two corners of a rectangular workpiece and maintain its position in a parallel relationship.

Briefly, in accordance with the present invention, there is provided an adjustable mandrel for supporting a workpiece. The mandrel includes a stationary first jaw having a body portion and a depending grasping leg, and a movable second jaw having a body portion mating with the body portion of the first jaw, and a depending grasping leg which mates with the grasping leg of the first jaw. The two grasping legs are parallel to each other. A coupling mechanism adjustably positions the movable second jaw with respect to the stationary first jaw while maintaining the parallel relationship between the grasping legs. The grasping legs can retain a workpiece positioned with respect to the grasping legs.

In an embodiment of the present invention, the coupling mechanism includes a captured screw which is rotatingly received in a fixed position in the body portion of the first jaw. The movable body portion of the second jaw threadingly floats along the screw mechanism upon rotation of the screw mechanism to thereby adjust the relative position of the movable second jaw with respect to the stationary second jaw.

A pair of guide rails project from the body portion of the first jaw and are received in parallel guide bores in the movable body portion of the second jaw to maintain accurate parallel alignment between the grasping legs.

The aforementioned objects, features and advantages of the present invention, will, in part, become obvious from the following more detailed description of the present invention, taken in conjunction with the accompanying drawings which form an integral part thereof.

BRIEF DESCRIPTION OF THE DRAWINGS

In the drawings:

FIG. 3 is an elevational exploded side view of the stationary first jaw and movable second jaw of the adjustable mandrel;

FIG. 4 is a partial elevational side view showing the grasping legs retaining a workpiece therebetween; and FIG. 5 is a partial elevational side view similar to that shown in FIG. 4, showing the grasping legs placed within a second workpiece to retain the second workpiece.

In the various figures of the drawings, like reference characters designate like parts.

DESCRIPTION OF THE PREFERRED EMBODIMENT

Figure 1:
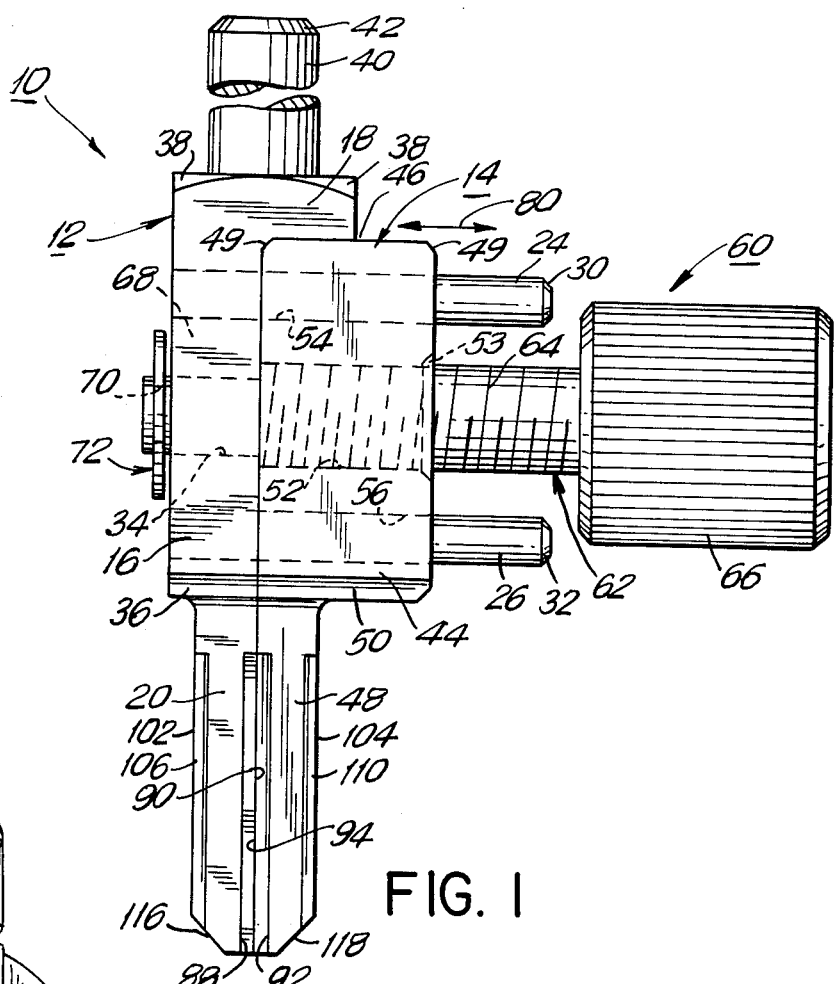
FIG. 1 is a side elevational view of the adjustable mandrel in accordance with the present invention, showing the movable second jaw abutting the stationary first jaw.

Referring now to the drawings, the adjustable mandrel shown generally at 10 comprises a stationary jaw 12 and a movable jaw 14. The stationary jaw 12 comprises a substantially rectangular body portion 16 with an overhanging lip portion 18. A depending grasping leg 20 extends downwardly from the body portion 16 and is offset to extend from one side 22 thereof.

A pair of parallel, spaced apart guide rails 24, 26 project from the internal surface 28 of the fixed body portion 16. The guide rails include chamfered distal ends 30, 32. An axial hole 34 is colinearly located between the guide rails 24, 26. A lower corner of the body portion 16 is chamfered at 36 and the lip portion 18 includes downwardly beveled corners 38.

Upwardly projecting from the lip portion 18 is an elongated shank portion 40 having a chamfered distal end 42. The shank portion 40 can be received within a conventional holding tool such as a jig or a suitable paralleling tool, as is well known in the art.

The movable jaw 14 includes a substantially rectangular body portion 44 of corresponding size and shape to the body portion 16. The height of the movable body portion 44 is such as to have its upper surface 46 slidably fit beneath the overhanging lip portion 18, as can best be shown in FIG. 1.

Depending from the movable body portion 44 is a grasping leg 48 positioned to matingly engage with the grasping leg 40. The upper corner edges and a lower corner edge of the movable body portion 44 are chamfered at 49 and 50, respectively.

An axial threaded bore 52 having a chamfered mouth 53 is provided at the approximate center of the movable body portion 44, the bore 52 being coaxial with the hole 34. Positioned in colinear relationship above and below the threaded bore 52 are a pair of guide holes 54, 56. The guide holes 54, 56 slidably receive the guide rails 24, 26, projecting from the stationary body portion 16.

A captured screw mechanism, shown generally at 60, couples the stationary jaw 12 and the movable jaw 14 in any adjustable relationship. The captured screw mechanism 60 includes a rotatable screw member 62 having an elongated cylindrical threaded portion 64. At one end of the threaded portion 64 is an enlarged knurled knob 66. A reduced diameter smooth shank portion 68 projects from the other end of the threaded portion 64. An annular groove 70 is provided adjacent the distal free end of the smooth shank portion 68.

Figure 2:
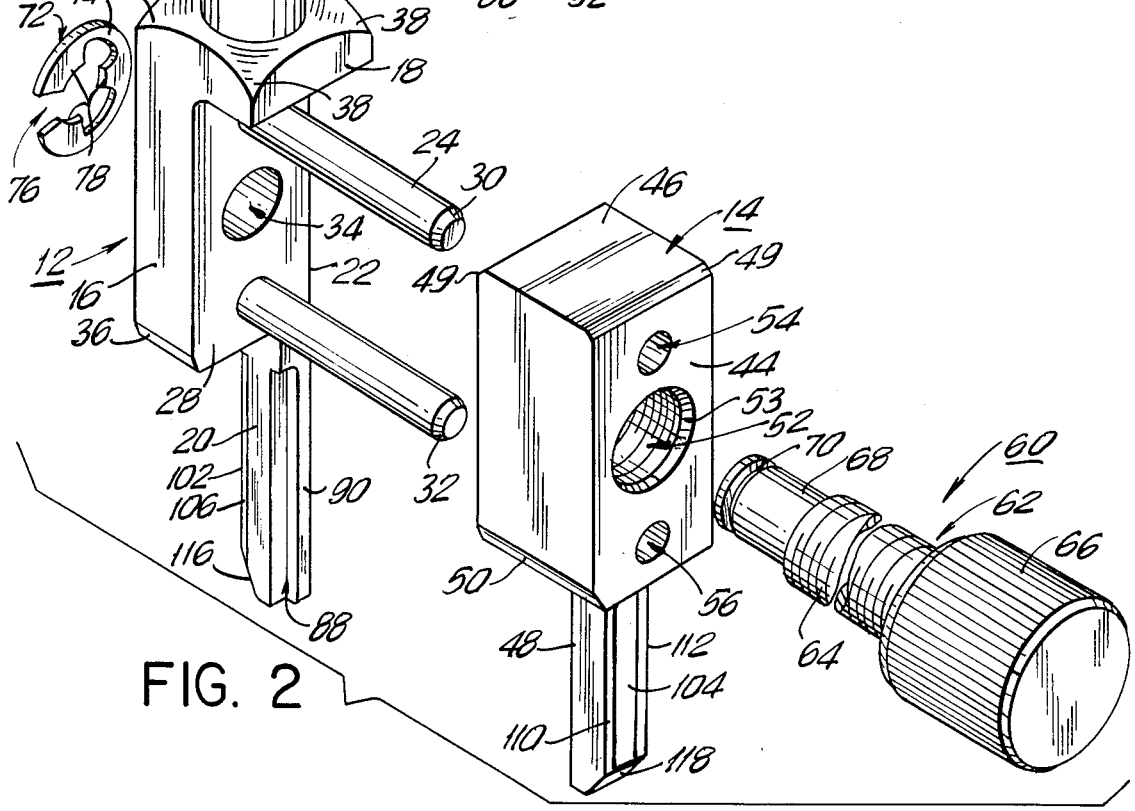
FIG. 2 is a perspective exploded view of the parts of the adjustable mandrel prior to assembly.

For retaining the screw member 62 in a captured rotatable relationship with the stationary jaw 12, there is provided a C-shaped retaining ring 72. The retaining ring 72 includes an annular peripheral rim 74 with a spaced gap 76, as best shown in FIG. 2. Inwardly protruding radial tabs 78 on the rim 74 provide engagement within the annular groove 70 of the screw member 62.

As best shown in FIGS. 1, 2 and 3, the adjustable mandrel is assembled by having the threaded bore 52 of the movable body portion 44 threadingly engaging the cylindrical threaded body portion 64 of the screw member 62 therein. The smooth shank portion 68 is rotatingly received in the axial smooth hole 34 in the stationary body portion 16. The screw member 62 is captured by having the tabs 78 of the retaining ring 72 engage in the annular groove 70 of the screw member 62, the ring 72 being positioned on the back side of the jaw 12. The guide rails 24, 26 of the jaw 12 extend through the guide holes 54, 56 of the jaw 14 for maintaining a parallel relationship between the movable jaw 14 and the stationary jaw 12, so that the grasping legs 20, 48 thereof are also in a parallel relationship.

By rotating the knurled knob 66 of the screw member 62, the movable jaw 14 is moved toward and away from the stationary jaw 12, as shown by the arrow 80 in FIG. 1. Thus, by moving the movable jaw 14 either into or out of engagement with the stationary jaw 12, simultaneously the grasping leg 48 on the movable jaw 14 is also moved either into or out of engagement with the grasping leg 20 on the stationary jaw 12 in the same direction and manner. Accordingly, the terms "stationary" and "movable" are associated with the rotation action of the screw member 62, where the jaw 12 always remains stationary relative to the horizontal position of the screw member 62, while the jaw 14 moves horizontally along the longitudinal length of the screw member 62.

As best shown in FIG. 4, a workpiece, such as a dental attachment device of the type described in the aforementioned patent, is shown at 82. The dental attachment device 82 can be retained between the opposing grasping legs 20, 48. As the knob 66 is rotated to bring the jaws 12, 14 together, as shown by the arrows 84, 86, the workpiece 82 will be grasped therebetween.

The movement of the movable jaw 14, into and out of engagement with the stationary jaw 12, is achieved along parallel lines. As heretofore mentioned, when utilizing a pair of bifurcated legs, as the legs are clamped together they pivot and, accordingly, the legs are brought together along an arcuate path and do not retain a parallel alignment therebetween. However, in the present case, the movable jaw 14 moves into an out of engagement with the stationary jaw 12 along a parallel relationship. Such parallel relationship is ensured by the presence of the guide rails 24, 26 which are parallel to each other and maintain the parallelism of the adjustable mandrel as described above.

Accordingly, the grasping legs 20, 48 will grasp a substantial length of the workpiece along parallel opposing outer sides thereof, and will retain such parallel relationship to apply the grasping force uniformly along the outer surfaces of the workpiece.

At the same time, the parallel lengths of the grasping legs 20, 48 are such that the grasping portion on the workpiece extended beyond that normally provided by the pivoting of the prior art grasping devices. This ensures a greater engagement path between the grasping legs 20, 48 and the workpiece to ensure a proper retention of the workpiece and a parallel relationship of the grasping legs resulting in proper placement of the workpiece with regard to the attachment thereof to other dental structures, in a manner set forth in the above mentioned patent.

In order to facilitate an accurate grasping and parallel relationship, a notch 88 is provided along the inner surface 90 of the grasping leg 20. A corresponding notch 92 is provided along the inner surface 94 of the movable grasping leg 48. In this manner, as can best be seen in FIG. 4, the grasping legs 20, 48 can grasp two corners of a rectangular workpiece 82 within the notches 88, 92 to assure the parallel relationship by grasping three sides of the workpiece and securing the workpiece in proper parallel relationship.

As can best be seen in FIG. 5, in addition to grasping the workpiece between the grasping legs 20, 48, the grasping legs 20, 48 can be moved outwardly, as shown by the arrows 86, 98, and grasp the interior of an arcuate cylindrical or other similarly shaped hollow workpiece 100. Rotating the knob 66 in the opposing direction moves the movable grasping leg 48 away from the stationary grasping leg 20. By inserting both grasping legs 20, 48 into the interior hollow space of the workpiece 100, the workpiece 100 can then be grabbed from its interior.

The ability to grasp a workpiece from the interior thereof is especially useful in connection with the dental retention members previously described. As stated above one of these dental members includes an elongated hollow cylindrical female portion, and through the use of the adjustable mandrel 10 of the present invention, grasping such female portion of the dental retention members is facilitated.

Since the interior surface of such cylindrical female dental member is arcuate, the exterior non-facing surfaces 102, 104 of the grasping legs 20, 48 can be beveled, at the corners 106, 108 of leg 20, and likewise the corners 110, 112 of leg 48 would be beveled. The beveling of the corners provides a closer proximation to the arcuate interior shape of the hollow workpiece 100, and facilitates the grasping of the workpiece 100 from its interior surface. The lower ends of both distal legs 20, 48 can be downwardly chamfered at 116, 118 so as to provide a guide for insertion into the hollow workpiece 100.

There has been disclosed heretofore the best embodiment of the present invention presently contemplated. However, it is to be understood, that various changes and modifications may be made thereto without departing from the spirit of the present invention.

What is claimed is:

1. An adjustable mandrel for supporting a workpiece, comprising:

a first jaw having a first body portion and a depending grasping first leg;

elongated shank means upwardly extending from said first body portion for insertion into a holding tool;

a second jaw having a mating second body portion and a depending mating grasping second leg;

coupling means for connecting, moving and adjustably positioning said second jaw with respect to said first jaw to thereby grasp a workpiece positioned with respect to said legs, said first jaw being connected in a stationary relationship with respect to said coupling means, and said second jaw being movable relative to said first jaw;

said coupling means including a captured screw member rotatingly secured in said first body portion, said second body portion threadingly receiving said screw member therein so that said second jaw moves along said screw member upon rotation of said screw member;

said screw member including a threaded cylindrical body portion being received in said second body portion, and enlarged knob at one end thereof for rotating said screw member, and a smooth smaller shank portion axially extending from the other end thereof, said smooth smaller shank portion being received in said first body portion;

an annular groove being provided in a distal end of said smooth smaller shank portion, and a retaining ring clamping into said annular groove to rotatably secure said screw member to said first body portion;

guide means for maintaining said first and second legs in a parallel relationship to each other during said moving and positioning of said second jaw with respect to said first jaw;

said guide means including guide rails projecting from said first body portion, and corresponding bores provided in said second body portion for receiving said guide rails so that said second jaw slides along said guide rails in a parallel relationship to said first jaw;

said guide rails including two guide rails respectively positioned above and below said captured screw member in co-planar relationship therewith; and said first and second legs including grasping means to grasp a first workpiece when positioned between said legs, and to alternatingly grasp a second workpiece when positioned around said legs;

said grasping means including parallel facing surfaces of said legs to grasp the first workpiece when positioned therebetween;

said grasping means also including parallel nonfacing surfaces of said legs to grasp the second workpiece when positioned therearound.

2. An adjustable mandrel as in claim 1, wherein said first body portion includes a smooth axial hole, said smooth shank portion being rotatably positioned within said axial hole with said threaded cylindrical body portion abutting against an interior side of said first body portion, said threaded cylindrical body portion having a diameter larger than said hole, said retaining ring being positioned on an exterior side of said first body portion to capture said screw member in said first jaw, and wherein said second body portion includes a coaxial threaded bore, said threaded cylindrical body portion being threaded within said axial threaded bore.

3. An adjustable mandrel as in claim 1, wherein said smooth shank portion has a smaller diameter than said threaded cylindrical body portion to define shoulder stop means therebetween for limiting extension of said screw member through said first body portion.

4. An adjustable mandrel as in claim 1, wherein said facing surfaces are provided with opposing elongated notches to define a U-shaped grasping portion for engaging two corners of the first workpiece.

5. An adjustable mandrel as in claim 1, wherein corner edges of said non-facing surfaces are beveled to facilitate grasping an interior surface of an arcuately shaped hollow portion of the second workpiece.

6. An adjustable mandrel as in claim 1, wherein said first jaw includes a lip portion extending beyond said first body portion, said second body portion slidably fitting beneath said lip portion.

7. An adjustable mandrel as in claim 1, wherein distal ends of said grasping legs are downwardly chamfered toward each other.

* * * * *